United States Patent
Jackson et al.

(10) Patent No.: US 6,585,755 B2
(45) Date of Patent: Jul. 1, 2003

(54) POLYMERIC STENT SUITABLE FOR IMAGING BY MRI AND FLUOROSCOPY

(75) Inventors: Gregg A. Jackson, San Francisco, CA (US); Stephen D. Pacetti, San Jose, CA (US)

(73) Assignee: Advanced Cardiovascular, Santa Clara, CA (US)

( * ) Notice: Subject to any disclaimer, the term of this patent is extended or adjusted under 35 U.S.C. 154(b) by 0 days.

(21) Appl. No.: 09/897,719

(22) Filed: Jun. 29, 2001

(65) Prior Publication Data

US 2003/0004563 A1 Jan. 2, 2003

(51) Int. Cl.[7] .................................................. A61F 2/06
(52) U.S. Cl. ...................................................... 623/1.15
(58) Field of Search ........................ 623/1.1, 1.15–1.23, 623/1.34, 1.38

(56) References Cited

U.S. PATENT DOCUMENTS

| | | | |
|---|---|---|---|
| 4,989,608 A | * | 2/1991 | Ratner ........................ 600/420 |
| 5,154,179 A | | 10/1992 | Ratner |
| 5,163,952 A | * | 11/1992 | Froix ......................... 623/1.18 |
| 5,603,722 A | * | 2/1997 | Phan et al. .................. 606/195 |
| 5,728,079 A | | 3/1998 | Weber et al. |
| 5,800,526 A | * | 9/1998 | Anderson et al. ............. 606/91 |
| 5,908,410 A | | 6/1999 | Weber et al. |
| 6,042,605 A | * | 3/2000 | Martin et al. ............... 623/1.13 |
| 6,340,367 B1 | * | 1/2002 | Stinson et al. ............. 623/1.34 |

FOREIGN PATENT DOCUMENTS

WO   WO 96/39103   12/1996

* cited by examiner

Primary Examiner—Michael J. Milano
Assistant Examiner—Tan-Uyen T. Ho
(74) Attorney, Agent, or Firm—Fulwider Patton Lee & Utecht, LLP

(57) ABSTRACT

An endovascular implant, stent or other medical device formed from a polymeric material, compounded with one or more materials to render the stent visible under both magnetic resonance imaging and x-ray based fluoroscopy procedures. The stent is adaptable to be placed in any body lumen and is contemplated to be a permanent or a biodegradable implant.

49 Claims, 4 Drawing Sheets

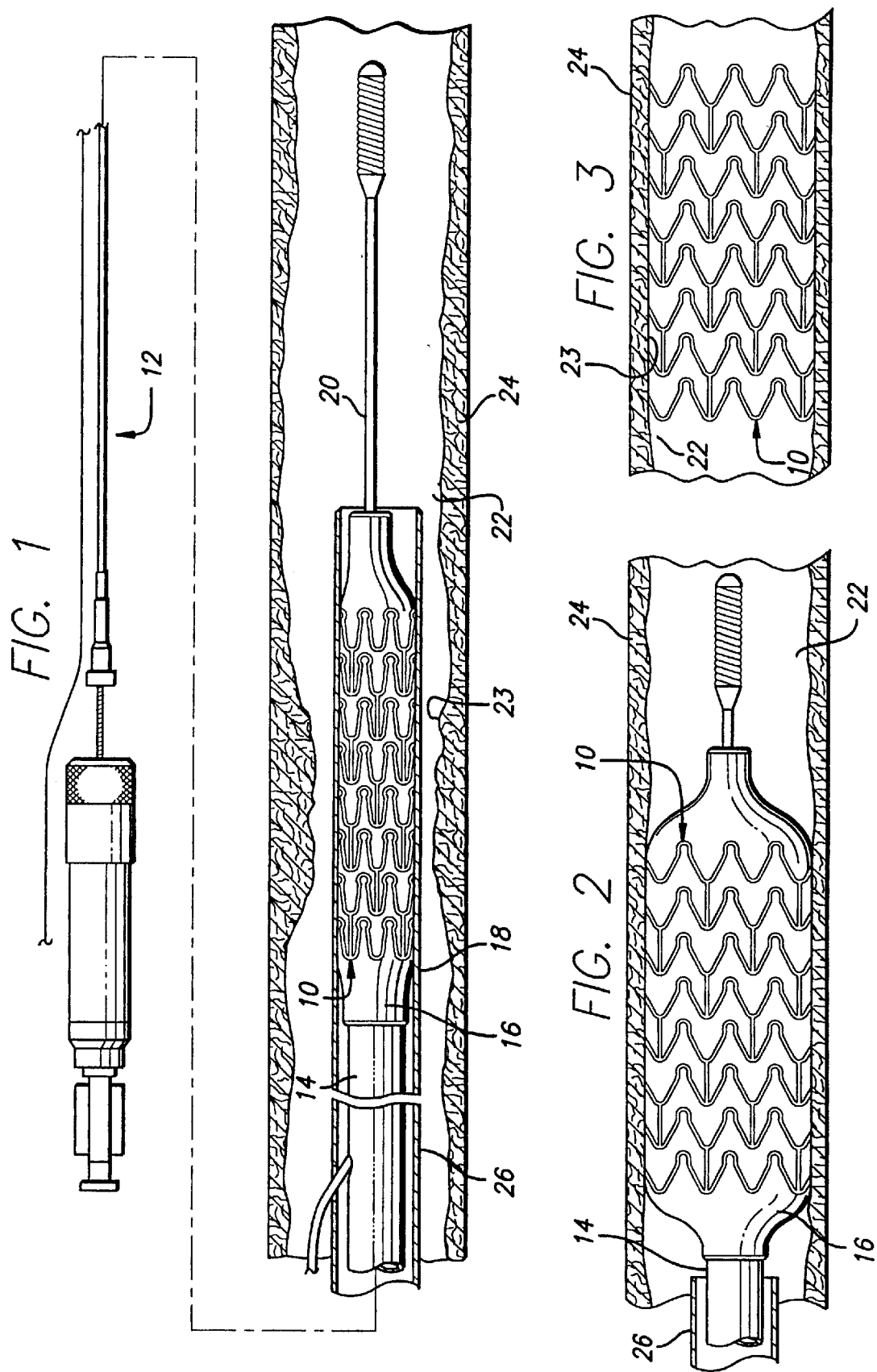

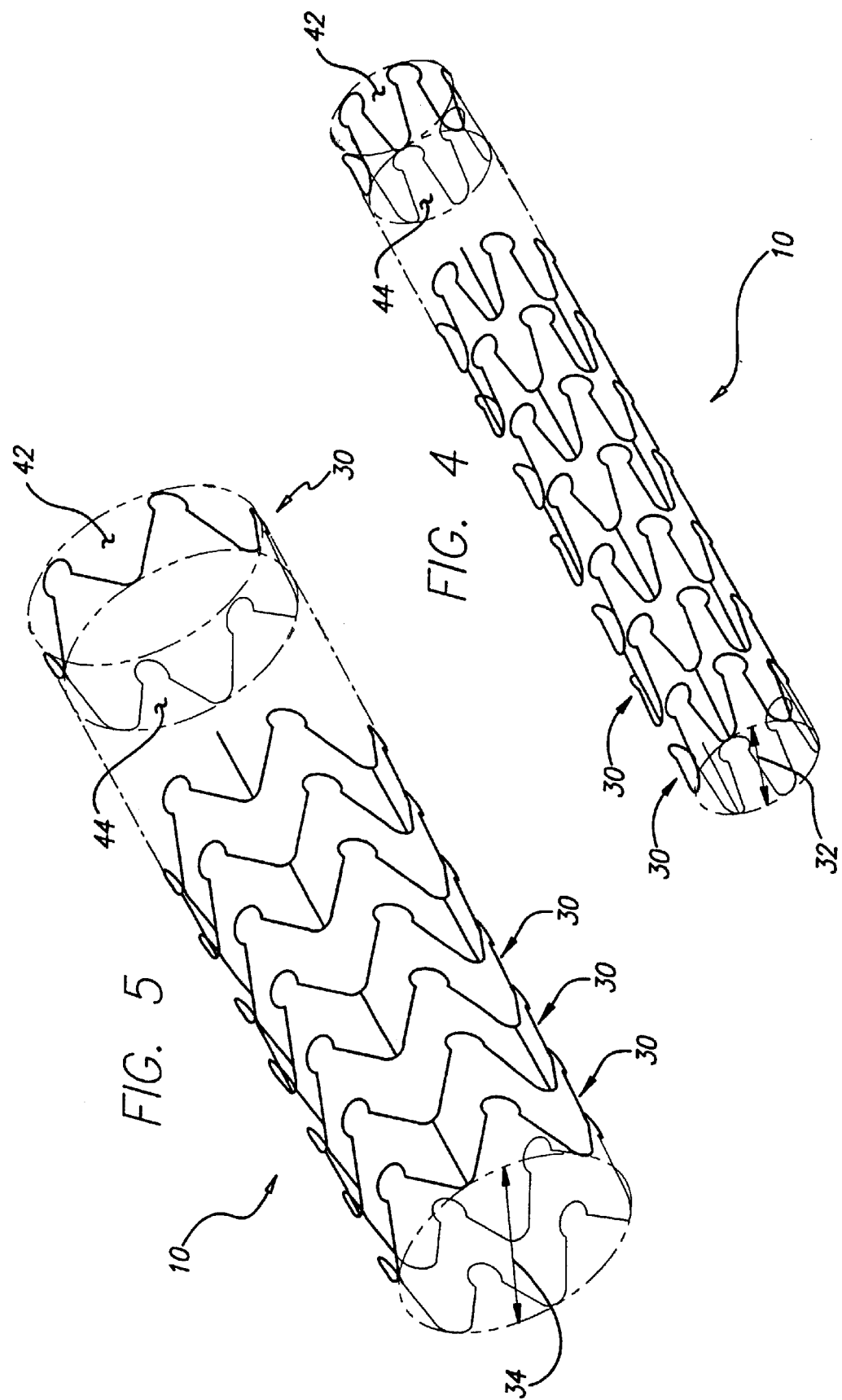

POLYMERIC STENT SUITABLE FOR IMAGING BY MRI AND FLUOROSCOPY

BACKGROUND OF THE INVENTION

This invention relates to endoprosthesis devices, generally called stents, and more particularly, to achieving desired visibility of such devices under magnetic resonance imaging (MRI) and fluoroscopy.

Stents are generally thin walled tubular-shaped devices composed of complex patterns of interconnecting struts which function to hold open a segment of a blood vessel or other body lumen such as a coronary artery. They also are suitable for supporting a dissected arterial lining or intimal flap that can occlude a vessel lumen. At present, there are numerous commercial stents being marketed throughout the world. These devices are typically implanted by use of a catheter which is inserted at an easily accessible location and then advanced through the vasculature to the deployment site. The stent is initially maintained in a radially compressed or collapsed state to enable it to be maneuvered through the lumen. Once in position, the stent is deployed. In the case of balloon expandable stents, deployment is achieved by inflation of a dilation balloon about which the stent is carried on a stent-delivery cathether.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, there is a requirement that a stent be radiopaque or fluoroscopically visible under x-rays. Accurate stent placement requires real time visualization to allow the cardiologist or interventional radiologist to track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. This is typically accomplished by the use of radiopaque materials in the construction of a stent, which allows for its direct visualization. The most common materials used to fabricate stents are stainless steel and nickel-titanium alloys, both of which are radiopaque. This factor, in combination with the relatively thin wall thickness (about 0.002 to 0.006 inch) of most stent patterns renders stents produced from these materials sufficiently radiopaque to be optimally visualized with x-ray based fluoroscopy procedures. Although both materials are generally regarded as being biocompatible, some recent concerns have arisen regarding the long term biocompatibility of stainless steel. Over time, nickel, a constituent element of most stainless steels, tends to leach from a stainless steel stent and in some sensitive patients will produce an allergic reaction. In addition, the chromium oxide layer present on the surface of stainless steel stents to prevent corrosion may have a tendency to degrade during long term use within the body.

Alternative, non-toxic, high density metals, such as tantalum, iridium, platinum, gold, and the like, have been used in prior art stents. However, these alloys can sometimes either be excessively radiopaque or may lack sufficient strength for recoil, radial strength requirements, and long-term use in a dynamic vascular setting. Stents constructed of highly radiopaque materials appear overly bright when viewed under a fluoroscope. This tends to overwhelm the image of the tissue surrounding the stent and obscures visualization of the stent lumen. Due to the lack of an appropriately radiopaque material, simply constructing a stent wholly out of a single material has heretofore not resulted in a stent with the optimal combination of mechanical properties and radiopacity. Thus, the art has moved in the direction of combining different materials to produce a mechanically sound, biocompatible and fluoroscopically visible stent. A number of such approaches have been developed. Typically such methods have focused on increasing the radiopacity or fluoroscopic visibility of stainless steel and nickel-titanium alloy stents.

One means frequently described for increasing fluoroscopic visibility is the physical attachment of radiopaque markers to the stent. Conventional radiopaque markers, however, have a number of limitations. Upon attachment to a stent, such markers may project from the surface of the stent, thereby comprising a departure from the ideal profile of the stent. Depending on their specific location, the marker may either project inwardly to disrupt blood flow or outwardly to traumatize the walls of the blood vessel. Additionally, galvanic corrosion may result from the contact of two disparate metals, i.e., the metal used in the construction of the stent and the radiopaque metal of the marker. Such corrosion could eventually cause the marker to separate from the stent which may be problematic should the marker be swept downstream within a vessel. Discrete stent markers cannot show the entire outline of the stent which is a preferred method to determine the optimal expansion of a stent over its entire length.

The radiopacity of stents has also been increased by plating or coating selected portions thereof with radiopaque material. However, a number of disadvantages are associated with this approach as well. When the stent is expanded certain portions undergo substantial deformation, creating a risk that cracks may form in the plating or coating causing portions of the plating to separate from the underlying substrate. This has the potential for creating jagged edges that may inflict physical trauma on the lumen wall tissue or cause turbulence in the blood flowing past the stent, thereby inducing thrombogenesis. Moreover, once the underlying structural material becomes exposed to an electrolytic solution such as blood, interfaces between the two disparate metals become subject to galvanic corrosion. Over time, galvanic corrosion may also lead to separation of the plated material from the underlying substrate.

X-ray based fluoroscopy is the current preferred modality for imaging stents during an intervention and for diagnostic assessment. However, in addition to the potential disadvantages stated above, other drawbacks may exist. Exposure to ionizing radiation and nephrotoxic iodinated contrast agents are intrinsic to the technique, as well as the need to wear leaded personal protective equipment. Alternatively, magnetic resonance imaging (MRI), produced by complex interactions of magnetic and radio frequency fields, does not suffer from these drawbacks and is actively being pursued to image stents in a diagnostic mode and, in the future, to guide stent based interventions. MRI has gained an increasing role in the diagnosis and assessment of human pathology. In patients undergoing MRI, there are numerous devices which are poorly seen, if they are visible at all, on the MR image artifact. The location and course of these implanted devices is usually of great clinical importance to assure their proper function and avoid complications that malposition can cause.

Due to their small size, current metal stents are sometimes difficult to see in fluoroscopy as they attenuate the x-ray beam very little. This is particularly true in very large, obese patients being imaged in lower end grade imaging systems. In MRI, the problem is that ferromagnetic and metallic based stents are difficult to see as they can create a large imaging artifact (a region of signal void or diminishment, which can extend beyond the stent boundaries). A plastic medical device, namely a polymeric stent, is particularly better for MRI as it is non-ferromagnetic and non-metallic. Indeed, a polymeric stent produces substantially no artifact at all. The signal used in most conventionally available MRI comes from the nuclear magnetic resonance of hydrogen nuclei. Polymers contain hydrogen atoms but these nuclei resonate at a frequency which is shifted from the water hydrogen signal from which the image is mainly derived. Moreover, the emitted RF signal from polymers is quite broad. Under MRI, polymers appear as a region of signal void that is the same size as the device and therefore, more clinically accurate. Unfortunately, this creates a situation analogous to fluoroscopy with a stent that is difficult to visualize. A solution to imaging a polymeric stent under MRI is to add a substance to the polymer to change its magnetic susceptibility. These materials are well known to those skilled in the art and consist of paramagnetic or ferromagnetic compounds, particles and fillers. By the choice of agent, and its concentration in the polymer, the size of the susceptibility artifact can be tuned.

MRI will not suddenly replace x-ray based fluoroscopy. Being new to the cardiology and interventional fields, and being an expensive technology, MRI utilization and implementation will vary by medical specialty, medical institution, and even on a country by country basis. Therefore, it seems likely that any stent produced for commercialization would ideally be imageable by both fluoroscopy and MRI. Although the paramagnetic or ferromagnetic compounds added for MRI visibility will increase the radiopacity of the polymer, it is not necessarily the case that a single concentration, of a single material, will give ideal visibility in both modalities.

However, MRI has the potential to supplant, and potentially substitute for fluoroscopy in the future. Stents which are more compatible with this imaging modality, or which have a dual functionality, may have a clinical performance benefit. Both the future of stent materials, and the imaging modalities used to visualize them are areas of intense research due to the clinical value and large market for stents, particularly coronary stents. Although metal alloy stents currently dominate the marketplace, polymer stents have potential advantages in the areas of hemocompatibility, biodegradability, and drug delivery.

What is needed therefore is a stent that overcomes the shortcomings inherent in previously known devices. Preferably, such a stent would be formed of a polymeric material, possess the required mechanical characteristics, and also be readily visible using MRI and x-ray based fluoroscopy procedures.

SUMMARY OF THE INVENTION

The present invention is directed to a stent that overcomes the shortcomings of previously known devices by embodying a polymeric material that is compounded with one or more materials to improve visibility under MRI and fluoroscopy.

The stent of the present invention may be made non-biodegradable with the use of an engineering polymer such as polyetheretherketone (peek), polyetherketone, polymethylmethacrylate, polycarbonate, polyphenylenesulfide, polyphenylene, polyvinylfluoride, polyvinylidene fluoride, polypropylene, polyethylene, poly (vinylidene fluoride-co-hexafluoropropylene), poly (ethylene-co-hexafluoropropylene), poly (tetrafluoroethyelene-co-hexafluoropropylene), poly (tetrafluoroethyelene-co-ethylene), polyethyleneterephthalate, polyimides and polyetherimide. For strength, the polymer may further contain reinforcements such as glass fiber, carbon fiber, Spectra™, or Kevlar™.

The stent of the present invention may be made biodegradable with the use of a polymer such as poly(L-lactide), polyglycolide, poly(D,L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes.

To confer a non-biodegradable stent with visibility under MRI, the stent of the present invention is compounded with an additive such as, but not be limited to, metal particles of gadolinium, iron, cobalt, nickel, dysprosium, dysprosium oxide, platinum, or other paramagnetic or ferromagnetic metals, gadolinium salts, gadolinium complexes, Gd-DTPA (gadolinium diethylenetriaminepentacetic acid), gadopentetate dimeglumine, compounds of copper, nickel, manganese, chromium, dysprosium and gadolinium. For a biodegradable stent, and in order to be visible under MRI, the stent of the present invention is compounded with substances that may be safely released in the body. Suitable metals would be chelates of gadolinium, or other paramagnetic metals such as iron or manganese.

For a non-biodegradable stent, in order to confer visibility under fluoroscopy, the stent of the present invention is compounded with an appropriate radiopacifier such as the powder of barium sulfate, bismuth subcarbonate, bismuth trioxide, bismuth oxychloride, tungsten, tantalum, iridium, gold, or other dense metal. To define a biodegradable structure, the stent of the present invention is compounded with a biodegradable radiopacifier that renders it visible under fluoroscopy and can be safely released in the body. Such radiopacifiers include particles of an iodinated contrast agent and bismuth salts.

It is to be recognized that the stent of the present invention can be self-expanding or balloon-expanded. Moreover, the present invention can be modified to be used in other body lumens including highly tortuous and distal vasculature as well as to create whole or portions of other medical devices or markers placed on such devices. Additionally, coating or other methods of applying the imageable material of the present invention are also contemplated.

These and other features and advantages of the present invention will become apparent from the following detailed description, which when taken in conjunction with the accompanying drawings, illustrate by way of example the principles of the invention.

BRIEF DESCRIPTION OF THE DRAWINGS

FIG. 1 is an elevational view, partially in section, depicting a stent embodying features of the invention and which is mounted on a balloon dilation catheter within an artery.

FIG. 2 is an elevational view, partially is section, similar to that shown in FIG. 1 depicting the stent expanded within the artery, so that the stent embeds within the arterial wall.

FIG. 3 is an elevational view, partially in section, showing the expanded stent implanted in the artery wall after withdrawal of the balloon catheter.

FIG. 4 is a perspective view of a stent embodying features of the invention, shown in an unexpanded state.

FIG. 5 is a perspective view of a stent embodying features of the invention shown, in an expanded state.

DETAILED DESCRIPTION OF THE PREFERRED EMBODIMENTS

Figure 6:
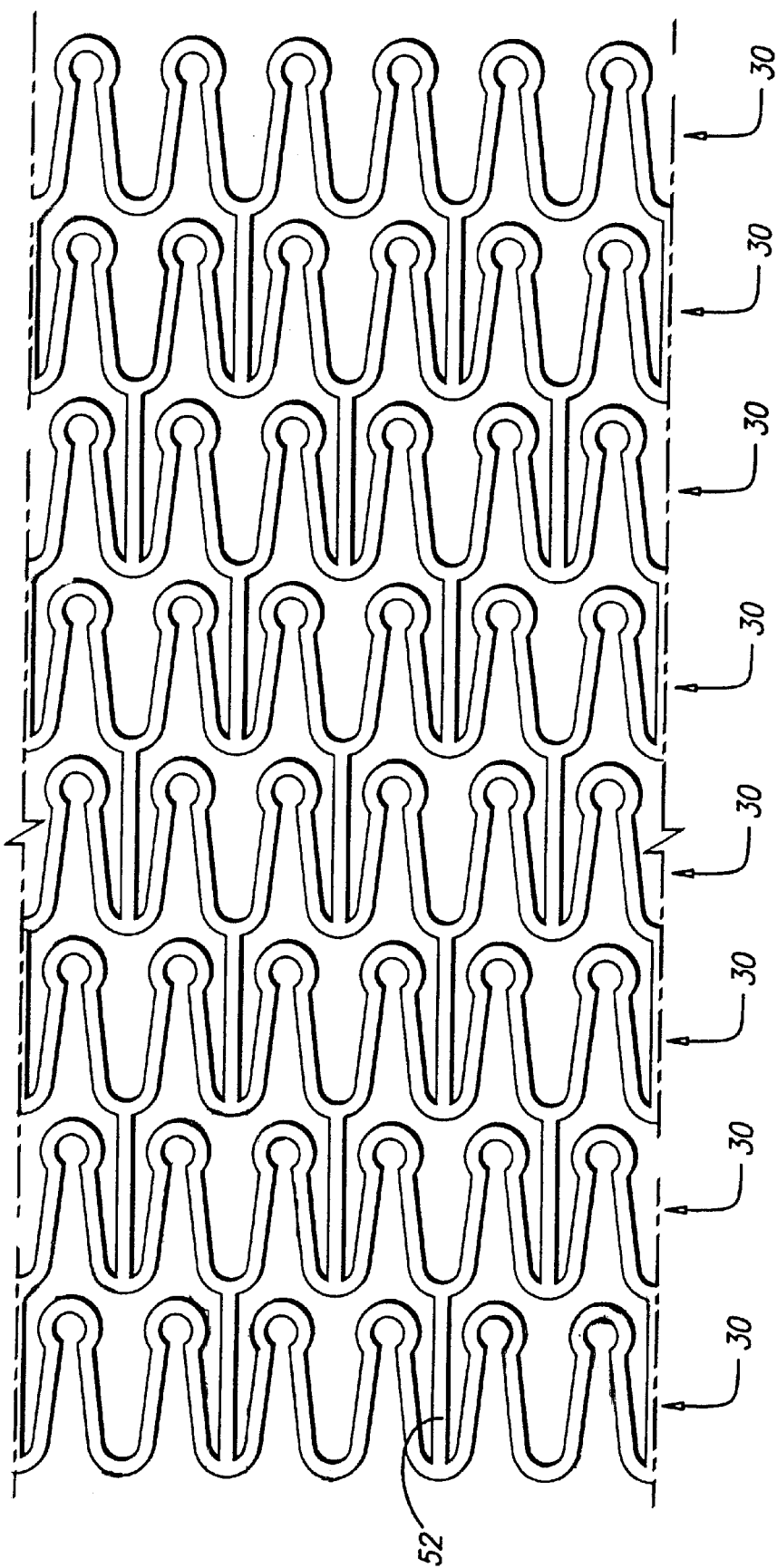
FIG. 6 is a plan view of a flattened section of the stent of the invention illustrating the pattern of the stent shown in FIG. 4.

The present invention is directed to a stent embodying a polymer into which one or more materials have been compounded to improve visibility under MRI and x-ray based fluoroscopy. The stent of the present invention can have virtually any configuration that is compatible with the body lumen in which it is implanted for the purpose of repairing the same. Typically, stents are composed of an intricate geometric pattern of circumferential and longitudinally extending members. These elements are commonly referred to as struts. Generally, the struts are arranged in patterns which are designed to contact the lumen walls of a vessel and to maintain patency of the vessel thereby. A myriad of strut patterns are known in the art for achieving particular design goals. A few of the more important design characteristics of stents are radial or hoop strength, expansion ratio or coverage area, and longitudinal flexibility. One strut pattern may be selected over another in an effort to optimize those parameters that are of importance for a particular application. An exemplary strut pattern will be described below.

In one exemplary embodiment, the stent of the present invention generally includes a plurality of cylindrical rings that are interconnected by a plurality of links. Each of the cylindrical rings making up the stent have a proximal end and a distal end and a cylindrical plane defined by a cylindrical outer wall surface that extends circumferentially between the proximal end and the distal end of the cylindrical ring. The cylindrical rings typically include a plurality of alternating peaks and valleys, where the valleys of one cylindrical ring are circumferentially offset from the valleys of an adjacent cylindrical ring. In this configuration, the connecting links attach each cylindrical ring to an adjacent cylindrical ring so that the links are positioned substantially within one of the valleys and attach the valley to an adjacent peak. Generally, the cylindrical rings are interconnected by at least one connecting link between adjacent cylindrical rings and each connecting link may be circumferentially offset from the previous connecting link in a preceding ring.

In one embodiment, the stent of the invention may be formed from a tube by laser cutting the pattern of cylindrical rings and connecting links in the tube. The stent also may be formed by laser cutting a flat polymeric sheet in the form of the rings and links, and then rolling the pattern into the shape of the cylindrical stent and providing a longitudinal weld to form the stent. Other methods of forming stents are well known and include chemically etching a flat polymeric sheet and rolling and then welding it to form the stent, or coiling a polymeric wire to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

The stent of the present invention achieves its MRI visibility objectives by embodying a polymer in combination with a material that generates a magnetic susceptibility artifact such as a paramagnetic, ferromagnetic, non-ferromagnetic, ferromagnetic, or superparamagnetic substance. A second, optional material may alternatively be employed to enhance the radiopacity of the device under x-ray based fluoroscopy and would contain a high atomic number element, preferably from the row of the periodic table coincident with the third row of the transition metal block. These materials may also be compounded into a polymeric coating placed on a polymeric stent. In the case of a polymeric stent that is intended to remain permanent in vasculature, the materials would be chosen to be biocompatible but not necessarily biodegradable. A biodegradable stent would require using agents that themselves are also biodegradable.

Suitable permanent non-biodegradable plastics for a stent would include engineering polymers such as polyetheretherketone (peek), polyetherketone, polymethylmethacrylate, polycarbonate, polyphenylenesulfide, polyphenylene, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate, polyimides and polyetherimides. For strength, the polymer may further contain reinforcements such as glass fiber, carbon fiber, Spectra™, or Kevlar™. Appropriate biodegradable polymers would include poly(L-lactide), polyglycolide, poly(D, L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes.

Additives to confer a permanent implant with MRI visibility for a permanent implant would include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, Gd-DTPA (gadolinium diethylenetriaminepentacetic acid), gadopentetate dimeglumine, compounds of copper, nickel, manganese, chromium, dysprosium and gadolinium. In the case of a biodegradable implant, the MRI agent should be highly biocompatible and excretable by the body. Candidates would be the chelates of gadolinium currently used as contrast agents. However, chelates of other paramagnetic metals such as iron or manganese are suitable.

Appropriate radiopacifiers for a permanent implant that is visible under fluoroscopy include powders of barium sulfate, bismuth subcarbonate, bismuth trioxide, bismuth oxychloride, tungsten, tantalum, iridium, gold, or other dense metals. A biodegradable stent requires biodegradable radiopacifiers. Examples of these can be drawn from the fields of radiology and nuclear medicine. Particles of an iodinated contrast agent, or bismuth salts are a possibility. Releasing a large number of nondegradable particles would likely result in an inflammatory response.

The potential need for two agents to be compounded into the polymeric stent to achieve visibility under both MRI and fluoroscopy procedures is due to the properties of the substances and the imaging devices involved. With a highly paramagnetic material, such as dysprosium oxide, a concentration in the polymer of only 0.01% to 2% by weight creates an adequate susceptibility artifact. However, for adequate radiopacity, even with a highly dense material like gold powder, a loading in the polymer on the order of 50% by weight is necessary. This is because stents are very thin, which creates a very short path length over which to absorb the x-rays, thus necessitating the high loading of radiopaque material. Due to the large density difference between a radiopaque material (gold, iridium, platinum, etc.) and a polymer, a high loading by weight corresponds to a small loading by volume. For example, an 80% loading of gold powder by weight in a typical polymer translates to only a 20% loading by volume. Stainless steel stents may require a ten-micron path length of gold (five microns per side) on an eighty-micron thick 316L stent for ideal radiopacity. For a given dimension, a polymeric strut is substantially less radiopaque than one of stainless steel. Consequently, a polymeric stent could require a larger effective gold path length on the order of seventeen microns on an eighty micron thick strut (8.5 microns per side) which equates to a 32% loading by volume of gold. In comparison, the MRI artifact is more determined by the concentration of marker powder, not the path length. If solid metal particles of gadolinium or dysprosium were used, the high loading needed for radiopacity would create too large of a MRI artifact.

The present invention applies to any endoluminal stent made of a polymer or equivalent material. Functionally, there is a limitation on the length, diameter, or strut thickness of the stent, and this is based on the performance features that are desired. The stent maybe used for coronary, neurological, carotid, renal, iliac, biliary, aortic, femoral, or other peripheral indication. The additives described may be distributed uniformly throughout the stent or confined to selected regions to serve as markers. The size of the particles are preferred to be on the order of 0.1 to 10 microns. If colloidal particles were used, and properly sealed inside the stent, the particles can be arbitrarily small (ten nanometers is possible). Large particles that occupy an appreciable fraction of the strut dimensions can compromise the mechanical properties of the stent. A polymeric coating may contain all, or a portion, of the additives. The stent may be of slotted tube design, meandered wire, or coil. It may be self expanding, expanded by the force of an angioplasty balloon, or other deployment device.

For background, it is instructive to briefly describe a typical stent implantation procedure and the vascular conditions which are typically treated with stents. Referring now to FIG. 1, a stent 10 of the present invention is shown mounted on a catheter 12 having a lumen 14 and an inflation member 16. The stent and catheter are shown inside a lumen 22 of an arterial vessel 24. The stent is shown positioned across a small amount of arterial plaque 23 adhering to the lumen of the artery. In some procedures, a stent is directly implanted without a prior procedure, such as balloon angioplasties. In other procedures, the plaque is the remainder of an arterial lesion which has been previously dilated or radially compressed against the walls of the artery or has been partially removed from the artery. Lesion dilation is typically accomplished by an angioplasty procedure, while lesion removal is typically accomplished by an atherectomy or rotoblation procedure. These and other procedures for the treatment of arterial lesions are well known to those skilled in the art.

With most lesion treatment procedures, the treated artery suffers a degree of trauma and in a certain percentage of cases may abruptly collapse or may slowly narrow over a period of time due to neointimal hyperplasia which is referred to as restenosis. To prevent either of these conditions, the treated artery is often fitted with a prosthetic device, such as stent 10 of the present invention. The stent provides radial support for the treated vessel and thereby prevents collapse of the vessel 24 and further provides scaffolding to prevent plaque prolapse within the lumen. The stent may also be used to repair an arterial dissection, or an intimal flap, both of which are commonly found in the coronary arteries, peripheral arteries and other vessels. In order to perform its function, the stent must be accurately placed across the lesion site. Therefore, it is critical that the stent be sufficiently visible so that the physician can visually locate the stent during the implantation procedure. Because the stent of the present invention can be made visible under MRI and fluoroscopy, it gives the physician the option of selecting the imaging modality most appropriate for the procedure.

With continued reference to FIG. 1, in a typical stent placement procedure, a guiding catheter (not shown) is percutaneously introduced into the cardiovascular system of a patient through the femoral arteries by means of a conventional Seldinger technique and advanced within a patient's vascular system until the distal end of the guiding catheter is positioned at a point proximal to the lesion site. A guide wire 20 and the stent-delivery catheter 12 of the rapid exchange type are introduced through the guiding catheter with the guide wire sliding within the stent-delivery catheter. The guide wire is first advanced out of the guiding catheter into the arterial vessel 24 and is directed across the arterial lesion. The stent-delivery catheter is subsequently advanced over the previously advanced guide wire until the stent is properly positioned across the lesion.

Referring now to FIG. 2, once in position, the dilation balloon 16 is inflated to a predetermined size to radially expand the stent 10 against the inside of the artery wall and thereby implant the stent within the lumen 22 of the artery. The balloon is then deflated to a small profile so that the stent-delivery catheter maybe withdrawn from the patient's vasculature and blood flow resumed through the artery.

Since the stent 10 is formed from an elongated tubular member, the profile of the stent is relatively flat in transverse cross-section, thus after implantation into the artery 24 as shown in FIG. 3, minimal interference with blood flow occurs. Eventually the stent ideally becomes covered with endothelial cell growth and restricted levels of neointimal hyperplasia. As should be appreciated by those skilled in the art, while the above-described procedure is typical, it is not the only method used in placing stents.

Typically, the stent 10 is laser cut from a solid tube. Thus, the stent does not possess discreet individual components. However, for the purposes of description it is beneficial to refer to the exemplary embodiment of the stent as being composed of cylindrical rings and connecting links. However, it is contemplated that various other forms of stents having generally tubular or bifurcated profiles can embody aspects of the present invention. For example, stents with a ratchet mechanism or a system of teeth and aperatures as described in U.S. Pat. Nos. 5,766,710 and 5,443,458 (the contents of each of which are hereby incorporated by reference) are types of expandable stents which could benefit from the present invention. Accordingly, a stent embodying the present invention can include teeth and corresponding catching structure which operates to maintain an expanded form. Moreover, polymer based stents embodying structure defined by a wire or ribbon coil or helix or a knitted mesh configuration are possible examples of self-expanding stents which also may benefit from the present invention by incorporating MRI and/or x-ray fluoroscopy imageable material. Another example of a self-expanding, polymeric-based stent is a tube that is folded longitudinally to assume a reduced profile and which expands upon removal of a device retaining the folded configuration. Certain of the described stents can be expanded either by pre-dilating the vessel or by balloon expansion.

It is also contemplated that a stent incorporating the present invention can embody a polymeric shape memory polymer, such as a methacrylate-containing polymer or an acrylate-containing polymer. The shape memory polymer can also be biodegradeable and may further include a therapeutic agent for controlled release within a body lumen. Moreover, the shape memory polymer can be a thermoplastic polymer or blend or a cross-linked thermoplastic polymer or blend. A state transition is caused by stimuli such as heat, change in pH or absorption of a separate component. Thermoset and light-activated polymers (e.g., UV light activated polymers) can be employed as well. Such polymers can be set or cured after expansion to provide sufficient mechanical strength to maintain patency of a vessel or body lumen. Heat can be used via a heating fluid in a balloon to accomplish curing or a light source can be passed through a catheter to irradiate the polymer for curing.

Referring now to FIGS. 4 and 5, the exemplary embodiment of the stent 10 is made up of a plurality of cylindrical rings 30 which extend circumferentially around the stent. The stent has an initial delivery diameter 32 as shown in FIG. 4, and an expanded or implanted diameter 34 as shown in FIG. 5. It is to be recognized that the stent of the present invention can be self-expanding or balloon expanded. Each cylindrical ring includes a cylindrical outer wall surface 42 which defines the outermost surface of the stent, and a cylindrical inner wall surface 44 which defines the innermost surface of the stent.

Referring now to FIG. 6, for the purpose of illustration only, the stent 10 is shown as a flat pattern so that the pattern of rings and links may be more clearly viewed. Interconnecting each cylindrical ring are a plurality of links 52. Typically, each adjacent ring will be connected by at least one connecting link. Each connecting link can be radially offset from the preceding and succeeding connecting links. Generally, radially offsetting the connecting links enhances uniform longitudinal flexibility of the stent, even though the links as shown are somewhat rigid.

In one embodiment of the present invention, particles of potassium iodide (80% by weight) and Gd-DPTA (2% by weight) are compounded into poly-L-lactide resin. This resin is melt spun into filaments. These filaments are thermally formed into corrugated rings that are then joined together to form a stent. The resulting stent is a largely self expanding biodegradable stent with biodegradable radiopaque and paramagnetic fillers.

Achieving good x-ray radiopacity and MRI visibility with a single filler is a challenge. In certain circumstances, 20% by volume loading (80% by weight of a metallic powder) is necessary for radiopacity. To keep the MRI artifact of the correct magnitude, an appropriate paramagnetic material would be used. Ferromagnetic materials would create too much artifact. A radiopaque metal such as palladium, with a volume magnetic susceptibility of $806 \times 10^6$ (SI), would have a chance of creating a reasonable susceptibility artifact at a 20% by volume loading. A plastic stent that is 20% by volume palladium should have a similar MRI artifact to an all tantalum stent. Tantalum stents are considered to have good MRI compatibility. Thus, in another embodiment of the present invention, particles of palladium (80% by weight) is compounded into polyaryletherketone resin (Victrex). The resulting resin is then melt spun into filaments. These filaments are formed into corrugated rings and joined together by thermal methods. The resulting stent is a self expanding permanent polymeric stent with a single filler for radiopacity and magnetic susceptibility.

It is to be recognized that aspects of the present invention are applicable to other medical devices. For example, the disclosed formulations can be employed to create a passive marker on an interventional or surgical device, such as a biopsy needle or other hand-held devices. Also, entire medical devices or portions thereof can embody the imageable material of the present invention and can have applications in laparoscopy (clip appliers) and heart valves. In one aspect, the present invention can be used to create an intravascular MRI (IVMRI) imaging catheter or a device combined with an active or passive tracking system. Such devices can be used alone or in combination with a stent of the present invention or other devices.

Specific formulations can be developed to create a device which is imageable when employing open or closed MRI systems or any of the current MRI imaging protocols (such as SMASH, FLASH, turbo FLASH), including an MR-compatible version of the POLARIS optical tracking system where a digitizer probe is used as an instrument probe. Additionally, specific formulations are contemplated for use with combined XMR-type systems that combine x-ray and MR systems along a common track or for that matter, with any future protocol that is either in development or will be developed in the future.

Figure 7:
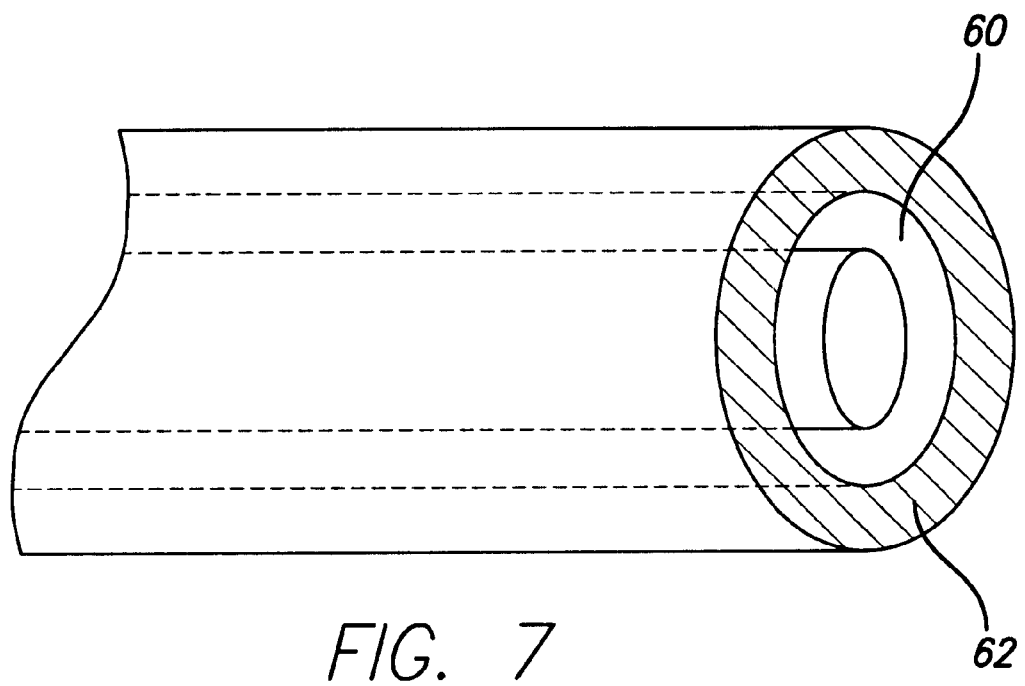
FIG. 7 is a partial cross-sectional view, depicting one approach to creating structure embodying the present invention.

It is also to be recognized that in addition to creating a stent or other medical device by compounding the imageable components together in a single blend, a number of other approaches can be taken. With reference to FIG. 7, there is shown a dual layer approach, wherein an inner polymer core 60 is provided, about which a layer of filler-radiopaque material and MR material 62 is configured. A tri-layered structure (not shown) can include, for example, an outer layer of 100% Pebax 72D (with or without 5% of a colorant, such as Pebax Blue), a middle layer of 100% Premier 1410, and an inner layer of 100% HDPE. Another approach that can be used is to combine a polymer core blended with radiopaque filler material, with an MR material.

Furthermore, various methods are contemplated for adding particulates to a polymer material. For example, particulates can be dip coated on a polymeric structure of a stent or other device. Moreover, particulates alone or blended with other materials can be added to the surface of a device by way of a plasma spray or etch or by employing thermal pressure or heat and pressure. Steriolithography and blow molding are other contemplated approaches. Also, the particulates can be mixed with a biocompatible epoxy resin, whereby the particulates are blended with another material and coated to the inner diameters, outer diameter or sides of structures defining the medical device or with a primacor solvent and applied to the subject structures. In any event, the particulates can be applied to an entire surface of a device or in a partial, spot-like manner or as stripes or a series of spots or stripes, or any other combination.

While only the presently preferred embodiments have been described in detail, as will be apparent to those skilled in the art, alternatives, additions, modifications and improvements maybe made to the device and method disclosed herein without departing from the scope of the invention. Accordingly, it is not intended that the invention be limited, except as by the appended claims.

What is claimed:

1. A stent for implantation within a body lumen of a patient, comprising:
   a body defined by a pattern of interconnected strut;
   a wherein the struts are made from polymeric material;
   a radiopaque material; and
   an MRI material designed to remain permanently in a body lumen;
   wherein the stent is imageable both under x-ray based fluoroscopy and MRI when placed in the body lumen and wherein the radiopaque material and the MRI material is compounded into the body of the stent.

2. The stent of claim 1, the body further comprising a helical shaped member defining a cylindrical profile.

3. The stent of claim 1, the body further comprising a knitted structure defining a cylindrical profile.

4. The stent of claim 1, wherein the body is self-expanding.

5. The stent of claim 1, wherein the body is expandable by a radial force.

6. The stent of claim 1, the body further comprising at least one ratchet mechanism.

7. The stent of claim 6, the ratchet mechanims further comprising a plurality of teeth configured to engage catching structure.

8. The stent of claim 1, the body further comprising a longitudinally extending slit.

9. The stent of claim 1, wherein the body can be folded longitudinally to assume a radially compressed configuration.

10. The stent of claim 1, wherein the polymeric material comprises at least one material from the group including polyetheretherketone (peek), polyetherketone, polymethylmethacrylate, polycarbonate, polyphenylenesulfide, polyphenylene, polyamide, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate and polyetherimide, glass fiber, carbon fiber, Spectra™, Kevlar™, poly(L-lactide), polyglycolide, poly(D, L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes.

11. The stent of claim 1, wherein the stent provides sufficient mechanical strength to maintain patency of the body lumen.

12. A stent for implantation within a vessel lumen of a patient, which is visible under magnetic resonance imaging and fluoroscopy, comprising:
   a pattern of struts interconnected to form a structure that contacts the lumen to maintain the patency thereof, wherein the struts are made from a polymeric material;
   a material designed to remain permanently in a body lumen, compounded into the stent, to generate a magnetic susceptibility artifact of the stent; and
   a material, compounded into the stent, to enhance radiopacity of the stent.

13. The stent of claim 12, wherein the polymeric material embodies shape memory characteristics.

14. The stent of claim 13, wherein the polymeric material contains methacrylate or acrylate.

15. The stent of claim 13, wherein the polymeric material is a thermoplastic polymer.

16. The stent of claim 13, wherein a state transition is caused by heat.

17. The stent of claim 13, wherein a state transition is caused by absorption.

18. The stent of claim 13, wherein a state transition is caused by a change in pH.

19. The stent of claim 13, wherein the polymeric material is a thermoset or light-activated polymer.

20. The stent of claim 12, wherein the polymeric material comprises at least one material from the group including polyetheretherketone (peek), polyetherketone, polymethylmethacrylate, polycarbonate, polyphenylenesulfide, polyphenylene, polyamide, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate and polyetherimide, glass fiber, carbon fiber, Spectra™, Kevlar™, poly(L-lactide), polyglycolide, poly(D, L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes.

21. The stent of claim 12, wherein the material compounded into the stent to generate a magnetic susceptibility artifact comprises at least one material from the group including metal particles of gadolinium, iron, cobalt, nickel, dysprosium, dysprosium oxide, platinum, palladium, cobalt based alloys, iron based alloys, stainless steel or other paramagnetic or ferromagnetic metals, gadolinium salts, gadolinium complexes, Gd-DTPA (gadolinium diethylenetriaminepentacetic acid), gadopentetate dimeglumine, compounds of copper, nickel, manganese, chromium, dysprosium and gadolinium, and chelates of gadolinium and other paramagnetic metals such as iron or manganese.

22. The stent of claim 12, wherein the material compounded into the stent to enhance radiopacity comprises at least one material from the group including powders of barium sulfate, bismuth subcarbonate, bismuth trioxide, bismuth oxychloride, tungsten, tantalum, iridium, gold, or other dense metals, particles of an iodinated contrast agent, and bismuth salts.

23. The stent of claim 12, wherein the material compounded into the stent may be distributed uniformly throughout the stent or confined to selected regions.

24. The stent of claim 12, wherein the stent is self-expanding.

25. The stent of claim 12, wherein the stent may be expanded by force.

26. The stent of claim 12, wherein the stent provides sufficient mechanical strength to maintain patency of the vessel lumen.

27. A stent for implantation within a vessel lumen of a patient, which is visible under magnetic resonance imaging and fluoroscopy, comprising:

a plurality of cylindrical rings interconnected to form the stent, each cylindrical ring having a first delivery diameter and a second expanded diameter;

each cylindrical ring having a proximal end and a distal end and a cylindrical wall extending circumferentially between the proximal end and the distal end of the cylindrical ring;

at least one connecting link attaching each cylindrical ring to an adjacent cylindrical ring;

the cylindrical rings and connecting links being formed from a polymeric material;

a first material designed to remain permanently in a body lumen to generate a magnetic susceptibility artifact of the stent; and a second material to enhance radiopacity of the stent;

wherein one of the first material and the second material is compounded into the stent.

28. The stent of claim 27, wherein the polymeric material comprises at least one material from the group including polyetheretherketone (peek), polyetherketone, polymethylmethacrylate, polycarbonate, polyphenylenesulfide, polyphenylene, ethers, polyamides, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate and polyetherimide, and polyetherimide, glass fiber, carbon fiber, Spectra™, Kevlar™, poly(L-lactide), polyglycolide, poly(D, L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes.

29. The stent of claim 27, wherein the first material first comprises at least one material from the group including metal particles of gadolinium, iron, cobalt, nickel, dysprosium, dysprosium oxide, platinum, palladium, cobalt based alloys, iron based alloys, stainless steel, or other paramagnetic or ferromagnetic metals, gadolinium salts, gadolinium complexes, Gd-DTPA (gadolinium diethylenetriaminepentacetic acid), gadopentetate dimeglumine, compounds of copper, nickel, manganese, chromium, dysprosium and gadolinium, and chelates of gadolinium and other paramagnetic metals such as iron or manganese.

30. The stent of claim 27, wherein the second material comprises at least one material from the group including powders of barium sulfate, bismuth subcarbonate, bismuth trioxide, bismuth oxychloride, tungsten, tantalum, iridium, gold, or other dense metals, particles of an iodinated contrast agent, and bismuth salts.

31. The stent of claim 27, wherein the first and second materials are distributed uniformly throughout the stent or confined to selected regions.

32. The stent of claim 27, wherein the stent is self expanding.

33. The stent of claim 27, wherein each cylindrical ring comprises a plurality of peaks and valleys.

34. The stent of claim 27, wherein the peaks of each cylindrical ring are axially aligned with the valleys of each adjacent cylindrical ring.

35. The stent of claim 27, wherein the first and second materials are both compounded into the stent.

36. The stent of claim 27, wherein one or more of the first or second materials are dip coated on the polymeric material.

37. The stent of claim 27, wherein one or more of the first or second materials are plasma sprayed on the polymeric material.

38. The stent of claim 27, wherein one or more of the first or second materials are plasma etched on the polymeric material.

39. The stent of claim 27, wherein one or more of the first or second materials are applied by thermal pressure on the polymeric material.

40. The stent of claim 27, wherein one or more of the first or second materials are applied by heat and pressure on the polymeric material.

41. The stent of claim 27, wherein one or more of the first or second materials are mixed with a biocompatible epoxy resin and coated on the polymeric material.

42. The stent of claim 27, wherein one or more of the first or second materials are blended with a primacor solution and applied on the polymeric material.

43. The stent of claim 27, wherein one or more of the first or second materials are applied only to portions of the polymeric material.

44. The stent of claim 27, wherein the stent is configured for use with SMASH, FLASH, or turbo FLASH MRI imaging protocols.

45. The stent of claim 27, wherein the stent is configured for use with open or closed MRI systems.

46. The stent of claim 27, wherein the stent is configured for use with combined XMR type systems that combine x-ray and MR systems along a common track.

47. The stent of claim 27, wherein the stent is configured for use with an MR-compatible version of an optical tracking system.

48. The stent of claim 27, wherein the stent provides sufficient mechanical strength to maintain patency of the vessel lumen.

49. A system including a medical device, the medical device comprising:

a body including struts made from a polymeric material;

a first material;

a second material;

wherein the first material guarantees a magnetic susceptibility artifact and the second material enhances the radiopacity of the device, and wherein one of the first material and second material is compounded into the body of the medical device.

* * * * *

UNITED STATES PATENT AND TRADEMARK OFFICE
CERTIFICATE OF CORRECTION

PATENT NO.     : 6,585,755 B2
DATED          : July 1, 2003
INVENTOR(S)    : Gregg A. Jackson et al.

It is certified that error appears in the above-identified patent and that said Letters Patent is hereby corrected as shown below:

<u>Title page,</u>
Item [73], Assignee, after "Cardiovascular" but before the ",", add -- Systems, Inc. --

<u>Column 11,</u>
Line 15, remove "a" before "wherein", and, add -- a -- after "from".

Signed and Sealed this

Eighteenth Day of November, 2003

JAMES E. ROGAN
*Director of the United States Patent and Trademark Office*